United States Patent [19]
Yamanaka et al.

[11] Patent Number: 5,892,100
[45] Date of Patent: Apr. 6, 1999

[54] METHOD FOR PRODUCING N-ACYL CARBAMATE

[75] Inventors: Eiji Yamanaka, Settsu; Masami Yabuta, Ibaraki; Satoshi Urano, Kyotanabe, all of Japan

[73] Assignee: Nippon Paint Co., Ltd., Osaka-Fu, Japan

[21] Appl. No.: 925,681

[22] Filed: Sep. 9, 1997

[30] Foreign Application Priority Data

Sep. 10, 1996 [JP] Japan ................................. 8-239049
Nov. 12, 1996 [JP] Japan ................................. 8-300110

[51] Int. Cl.$^6$ ................................................. C07C 261/00
[52] U.S. Cl. ........................... 560/157; 560/162; 560/165; 560/166; 560/167; 544/168; 546/226; 549/496; 564/48; 564/56; 564/60; 564/62; 564/255
[58] Field of Search ................................ 560/157, 162, 560/165, 166, 167; 544/168; 546/226; 549/496; 564/62, 255, 48

[56] References Cited

U.S. PATENT DOCUMENTS 5,187,306  2/1993  Tsuboniwa et al. ..................... 560/157
5,606,096  2/1997  Yamanaka et al. ..................... 560/157

Primary Examiner—Samuel Barts
Attorney, Agent, or Firm—Wenderoth, Lind & Ponack, L.L.P.

[57] ABSTRACT

The present invention provides a method for producing N-acyl carbamate in high yield. The method of the present invention comprises the step of reacting an unsaturated acid halide with a carbamate in the presence of a hindered amine. Another method of the present invention comprises the step of reacting a N,N-diacyl carbamate with an active hydrogen compound.

8 Claims, No Drawings

METHOD FOR PRODUCING N-ACYL CARBAMATE

FIELD OF THE INVENTION

The present invention relates a method for producing N-acyl carbamate.

BACKGROUND OF THE INVENTION

The present inventors have developed N-acyl carbamate represented by the formula:

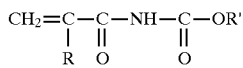

wherein, R is hydrogen or a lower alkyl group and R' is a residual group obtained by removing a hydroxyl group from a monovalent alcohol; in Japanese Patent Laid-Open Publication No. 275259/1986, 275260/1986, 275270/1986 and 66563/1992, and also have developed the use thereof.

This N-acyl carbamate is prepared by reacting the compound which has the metal salt of an amide group represented by the formula:

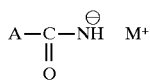

wherein, A is a 1-alkylvinyl group or an alkoxy group, and $M^+$ is a metal cation; with the compound represented by the formula:

wherein, X is halogen, and B is an alkoxy group or a 1-alkyl vinyl group; in an inert solvent, as described in Japanese Patent Laid-Open Publication No. 66563/1992. In this method, aprotic solvents such as a hydrocarbon, ether, ester, ketone, nitrile and the like, are exemplified as the inert solvent.

Japanese Patent Laid-Open Publication No. 279666/1990 discloses a method for producing an acyl carbamate in which an acid amide and a dicarbonate are reacted in the presence of a metal salt. 2-Butanol is exemplified as a solvent.

However, especially in case of producing N-methacryloyl carbamate, some problems may occur. For example, yield of the product decreases depending on a kind of the base compound used. When a metallic base is used as the base compound, the salt thereof with amide or the metal salt formed has low solubility in an organic solvent, and yield of the product extremely lowers. On the other hand, when an organic base is used as the base compound, the salt thereof is soluble in an organic solvent. However, N,N-dimethacryloyl carbamate is mainly produced, and an objective compound, N-methacryloyl carbamate is obtained in low yield.

SUMMARY OF THE INVENTION

The object of the present invention is to provide a method for producing N-acyl carbamate in high yield, and a method for producing N-acyl carbamate by using N,N-diacyl carbamate which is a by-product in case of producing the N-acyl carbamate, as a raw material.

The present invention provides a method for producing the N-acyl carbamate represented by the formula:

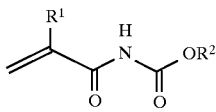

wherein, $R^1$ is a hydrogen atom or a lower alkyl group, and $R^2$ is a residual group obtained by removing a hydroxyl group from a monovalent alcohol; which comprises the step of reacting the unsaturated acid halide represented by the formula:

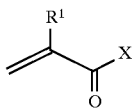

wherein, $R^1$ is a hydrogen atom or a lower alkyl group, and X is a halogen atom; with the carbamate represented by the formula:

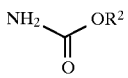

wherein, $R^2$ is a residual group obtained by removing a hydroxyl group from a monovalent alcohol; in the presence of the hindered amine represented by the formula:

wherein, $R^3$ each independently represents an alkyl group having up to 12 carbon atoms, and at least two of them represent a secondary alkyl group having 3 to 12 carbon atoms.

The present invention further provides a method for producing the N-acyl carbamate represented by the formula:

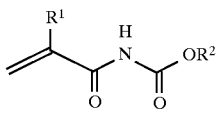

wherein, $R^1$ is a hydrogen atom or a lower alkyl group, and $R^2$ is a residual group obtained by removing a hydroxyl group from a monovalent alcohol; which comprises the step of reacting the N,N-diacyl carbamate represented by the formula:

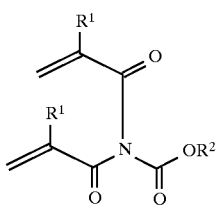

wherein, $R^1$ is a hydrogen atom or a lower alkyl group, and $R^2$ is a residual group obtained by removing a hydroxyl group from a monovalent alcohol; with the active hydrogen compound represented by the formula:

wherein, X is a nitrogen atom or an oxygen atom, Y is a hydrogen atom, a linear or cyclic alkyl group, an aryl group, aralkyl group, alkenyl group, alkynyl group, alkylcarbonyl group, or alkoxycarbonyl group, having 1 to 18 carbon atoms, which may have a substituent, and n is an integer from 1 to k, wherein k indicates a valence of the X atom.

DETAILED DESCRIPTION OF THE INVENTION

In the first method for producing N-acyl carbamate of the present invention, an unsaturated acid halide and a carbamate are reacted in the presence of a hindered amine.

As the unsaturated acid halide which can be used in the present invention, there are exemplified the compounds represented by the formula (1), wherein $R^1$ is a hydrogen atom or an alkyl group having from 1 to 8, preferably from 1 to 6 carbon atoms, and X is chlorine or bromine.

Specific examples of $R^1$ include a hydrogen atom; saturated or unsaturated aliphatic alkyl groups such as methyl, ethyl, propyl, isopropyl, butyl, pentyl and hexyl; and preferably include a hydrogen atom or methyl group.

Specifically, methacrylic chloride and acrylic chloride are exemplified.

As the carbamate which can be used in the present invention, there are exemplified the compounds represented by the formula (2), wherein $R^2$ is a hydrogen atom or an alcohol residual group having up to 20 carbon atoms. Preferably, $R^2$ is a linear or cyclic alkyl group having from 1 to 18, preferably from 1 to 6 carbon atoms, or $R^2$ is an aryl group, aralkyl group, alkenyl group, alkynyl group, alkylcarbonyl group or alkoxycarbonyl group, having from 1 to 18, preferably from 1 to 6 carbon atoms, which may have a substituent.

Specific examples of $R^2$ include primary alkyl groups having up to 14 carbon atoms such as methyl, ethyl, 1-propyl, 1-butyl, isobutyl, 1-pentyl, 1-hexyl, 1-heptyl, 1-octyl, 1-nonyl, 1-decyl, 1-undecyl, 1-dodecyl, hexadecyl, 1-octadecyl, isodecyl, 2-methyl-1-propyl, neopentyl, 2-methyl-1-butyl- 3-methyl-1-butyl, 3-methyl-2-butyl, 2-ethyl-1-butyl, 3,3-dimethyl-1-butyl, 2,3-dimethyl-2-butyl, 3,3-dimethyl-2-butyl, 2-ethyl-i-hexyl, methoxyethyl, ethoxypropyl, butoxyethyl and hexyloxyethyl;

secondary alkyl groups having up to 14 carbon atoms such as 2-propyl, 2-butyl, 2-pentyl, 2-hexyl, 2-heptyl, 2-octyl, cyclohexyl, 2-methylcyclohexyl, isopropyl, 2-ethylhexyl, isobutyl; sec-butyl;

tertiary alkyl groups having up to 20 carbon atoms such as tert-butyl, tert-amyl, tert-pentyl, 1,1-dimethyl-3-butanoyl, 3-methyl-3-pentyl, 1,1-dimethylbenzyl and 3-ethyl-3-pentyl;

unsaturated aliphatic alkyl groups having up to 20 carbon atoms such as allyl, 2-methylallyl and oleyl, saturated and unsaturated alicyclic alkyl groups having up to 20 carbon atoms such as cyclopentyl, cyclohexyl, methylcyclohexyl, cyclooctyl, cyclododecenyl, norbornane, boronyl, adamantyl, tetrahydrofurfuryl, cyclohexenyl, norbornyl and furfuryl;

aryl groups having up to 20 carbon atoms such as phenyl, (o)-ethylphenyl, 4-methoxyphenyl, 2,6-di-tert-butylphenyl, 4-methylphenyl, benzyl, phenetyl, (p)-chlorophenyl, (p)-bromophenyl, naphthyl and ethoxyphenyl; and alkoxyalkyl groups having up to 20 carbon atoms such as 2-ethoxyethyl, 2-methoxyethyl, 2-butoxyethyl, 2-isopropoxyethyl, 2-benzyloxyethyl, 2-phenoxyethyl, 2-(2-methoxy)ethoxyethyl, 2-(2-butoxy)ethoxyethyl, 2-(2-hexyloxy)ethoxyethyl, 2-(2-benzyloxy) ethoxyethyl, 2-(2-phenoxy)ethoxyethyl, and 2-hexyloxyethyl. Preferable $R^2$ is the secondary alkyl group.

Preferable examples of the carbamate include 2-butyl carbamate, 2-octyl carbamate, cyclohexyl carbamate, 2-methylcyclohexyl carbamate, butoxyethyl carbamate, ethoxyethyl carbamate and 2-hexyloxyethyl carbamate.

In a reaction of the first method, the unsaturated acid halide and the carbamate are used in an amount of from 0.5 to 3.mol, preferably from 0.8 to 2 mol per one mol of the carbamate.

The hindered amine used in the present invention is a tertiary amine in which rotation of a substituent is restrained, such as that represented by the formula:

wherein, $R^3$ each independently represents an alkyl group having up to 12 carbon atoms, and at least two of them represent a secondary alkyl group having 3 to 12 carbon atoms.

Specific examples of $R^3$ include a hydrogen atom; primary alkyl groups such as methyl, ethyl, propyl, isopropyl and butyl; and secondary alkyl groups such as isobutyl, sec-butyl, cyclohexyl, and isopropyl.

Preferable examples of the hindered amine include dicyclohexylmethyl amine, dicyclohexylethyl amine, diisopropylethyl amine, butyldicyclohexyl amine, diisopropyl-2-chloroethyl amine, butyldiisopropyl amine and the like. These can be used alone or in combination.

The amount used of these hindered amine is not particularly restricted, and preferably from 0.5 to 3 mol per one mol of the carbamate.

The reaction of the unsaturated acid halide with the carbamate of the present invention can be conducted in the presence or absence of a solvent. The solvent is generally used in an amount up to 10-fold of the weight of the carbamate. The kind of the solvent is not particularly restricted provided it is an inert solvent which sufficiently dissolves the reactants and the reaction product, and does not react with them.

Specific examples of the solvent may be suitably selected from aliphatic hydrocarbons such as pentane, hexane, heptane and octane; aromatic hydrocarbons such as benzene, toluene, xylene and tetralin; alicyclic hydrocarbons such as cyclohexane, methylcyclohexane and decalin; hydrocarbon-based solvents such as petroleum ether and petroleum benzine; halogenated hydrocarbon-based solvents such as carbon tetrachloride, chloroform, 1,2-dichloroethane, chlorobenzene and dichlorobenzene; ether-based solvents such as ethyl ether, isopropyl ether, anisole, dioxane, tetrahydrofuran (THF), glyme and diglyme; ketone-based solvents such as acetone, methyl ethyl ketone, methyl isobutyl ketone, cyclohexane, acetophenone and isophorone; ester-based solvents such as ethyl acetate and butyl acetate; amide-based solvents such as dimethylformamide (DMF) and methylpyrrolidone; acetonitrile; dimethyl sulfoxide; and the like.

These may be used alone or in combination. Among these solvents, the organic solvents which has a dielectric constant from 1.5 to 4, specifically, hexane, cyclohexane, heptane, dioxane, toluene and the like are particularly preferable, in the present invention.

In general, this reaction is conducted at a temperature from 50° to 150° C., preferably from 70° to 120° C. for 2 to 10 hours. When the reaction temperature is less than 50° C., yield of the product becomes low, since the reaction does not progress sufficiently. On the other hand, when over 150° C., yield of the product becomes low, since a side reaction occurs.

In the second method for producing N-acyl carbamate of the present invention, N,N-diacyl carbamate and an active hydrogen compound are reacted.

The N,N-diacyl carbamate used in the present invention is a by-product which is generated in case of producing the N-acyl carbamate. After the reaction, an isolated and purified N,N-diacyl carbamate can be used in the present invention.

Therefore, in the formula (4), $R^1$ and $R^2$ are the same as defined above.

The N,N-diacyl carbamate may be synthesized separately, as explained specifically in the following examples. A synthesis method of the N,N-diacyl carbamate is well-known to those skilled in the art, and any of the method can be used.

The active hydrogen compound used in the present invention is, for example, a compound having at least one hydrogen atom bonded to a hetero atom, represented by the formula:

$$H_n XY_{k-n} \qquad (5)$$

wherein, X is a nitrogen or an oxygen atom, Y is a hydrogen atom, a linear or cyclic alkyl group, an aryl group, aralkyl group, alkenyl group, alkynyl group, linear or cyclic alkylcarbonyl group, arylcarbonyl group, aralkylcarbonyl group, alkenylcarbonyl group, alkynylcarbonyl group, or alkoxycarbonyl group, having 1 to 18 carbon atoms, which may have a substituent, and n is an integer from 1 to k, wherein k indicates a valence of the X atom.

The preferable active hydrogen compound is the amine compound represented by the formula:

$$H_m NR^4{}_{3-m} \qquad (6)$$

wherein, $R^4$ is a linear or cyclic alkyl group, an aryl group, aralkyl group, alkenyl group or alkynyl group, having 1 to 18 carbon atoms, which may have a substituent, and m is an integer from 1 to 3.

Examples of the active hydrogen compound include ammonia; primary amines such as methylamine, ethylamine, 1-propylamine, 1-butylamine, 1-pentylamine, 1-hexylamine, 1-heptylamine, 1-octylamine, 1-nonylamine, 1-decylamine, 1-undecylamine, 1-dodecylamine, hexadecylamine, 1-octadecylamine, isopropylamine, sec-butylamine, isobutylamine, 1-methylbutylamine, 1-ethylpropylamine, tert-butylamine, ter-amylamine, tert-octylamine, 3-methoxypropylamine and 2-chloroethylamine; secondary amines such as dimethylamine, diethylamine, dipropylamine, dibutylamine, dipentylamine, dihexylamine, diheptylamine, dioctylamine, dinonylamine, didecylamine, diundecylamine, didodecylamine, N-methylpropylamine, N-methylisopropylamine, N-methylbutylamine, N-methyl-tert-butylamine, N-methylhexylamine, N-isopropylhexylamine, allylcyclohexylamine, bis(2-methoxyethyl)amine, diisopropylamine, di-sec-butylamine, diisobutylamine, di-tert-butylamine, di-tert-amylamine, di-tert-octylamine, dicyclopentylamine, dicyclohexylamine, dicyclooctylamine, dicyclohexenylamine, pyrrolidine, piperidine and morpholine; amino alcohols such as ethanolamine, 2-(methylamino)ethanol and diethanolamine; alcohols such as methanol, ethanol, propanol, isopropanol, butanol, sec-butanol, hexanol, octanol, decyl alcohol, dodecanol, pentadecanol, octadecanol, neopentyl alcohol, amyl alcohol, 2-ethylhexanol, allyl alcohol, crotyl alcohol, cyclohexanol, phenol, benzyl alcohol, phenetyl alcohol, N,N-dimethylethanolamine and 2-chloroethanol; amide compounds such as acetoamine, propioneamide, isobutylamide, trimethylacetoamide, cyclohexanecarboxyamide and chloroacetoamide; and the like.

The carbamate represented by the formula (2) can be also used as the active hydrogen compound. In this case, $R^2$ is the same as defined above, and preferably is the same as $R^2$ of the N,N-diacyl carbamate used as a raw material.

When a carbamate is used as the active hydrogen compound, it is preferable to use a catalyst. Examples of the preferable catalysts include protonic acids such as p-toluenesulfonic acid, phosphoric acid, methanesulfonic acid, sulfuric acid, hydrochloric acid, phthalic acid, succinic acid, chloroacetic acid, acetic acid and trifluoroacetic acid; Lewis acids such as dibutyltin dilaurate, titanium tetraisopropoxide, copper chloride, zinc chloride and aluminum chloride; and the like.

The catalyst is used in an amount from 0.1 to 20% by mol, preferably from 1 to 10% by mol based on the N,N-diacyl carbamate.

Specific examples of the carbamate suitably used include methyl carbamate, ethyl carbamate, butyl carbamate, methoxyethyl carbamate, butoxyethyl carbamate, hexyloxyethyl carbamate, 2-ethylhexyl carbamate and the like.

In a reaction of the second method, it is preferable to use the active hydrogen compound in the amount equivalent to the N,N-diacyl carbamate. When the amount used of the active hydrogen compound is over the equivalent amount of the N,N-diacyl carbamate, the active hydrogen compound remains after the reaction. Therefore, quality of the resulting N-acyl carbamate becomes poor, and separation and purification are required. Substantially the same problems may also occur when an excess amount of the N,N-diacyl carbamate is used, based on an amount of the active hydrogen compound.

The reaction of the N,N-diacyl carbamate with the active hydrogen compound can be conducted in the presence or absence of a solvent. The solvent optionally used is not particularly restricted provided it sufficiently dissolves the reactants and the reaction product.

Specific examples of the solvent include hydrocarbon-based solvents such as pentane, hexane, heptane, toluene, xylene, cyclohexane, decalin and petroleum ether; halogen-based solvents such as dichloroethane and dichlorobenzene; ether-based solvents such as dioxane, diglyme and anisole; ketone-based solvents such as methylisobutyl ketone, cyclohexanone and isophorone; and ester-based solvents such as butyl acetate; and the like.

This reaction is generally conducted at a reaction temperature from 60° to 180° C., preferably from 80° to 120° C. for 0.5 to 10 hours, preferably 1 to 3 hours.

The scheme of the reaction is shown below.

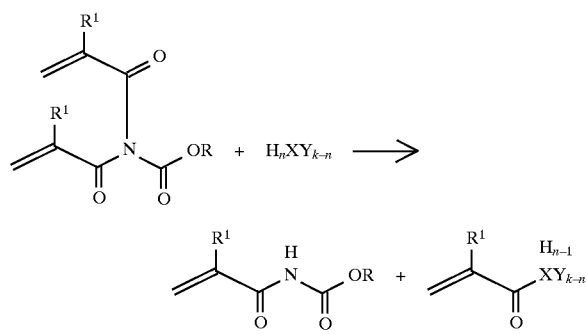

EXAMPLES

The following examples further illustrate the present invention in detail but are not to be construed to limit the scope thereof.

Example 1

Into a 100 ml reaction vessel were charged 8.7 g of 2-octyl carbamate, 5.3 g of methacryloyl chloride, 9.8 g of dicyclohexylmethylamine and 25 g of hexane, and they were heated at 80° C. with stirring, reacted for 6 hours and cooled. The reaction mixture was analyzed by $^1$H-NMR to find that it contained 10% of 2-octyl N,N-dimethacryloyl carbamate which was the by-product, based on the amount of 2-octyl N-methacryloyl carbamate which was the intended product.

The reaction mixture was then filtered and concentrated, and the concentrate was purified by column chromatography, to obtain 6.0 g of a white solid having a melting point of 41° C. The yield was 50%.

Example 2

Into a 100 ml reaction vessel were charged 7.3 g of cyclohexyl carbamate, 5.3 g of methacryloyl chloride, 9.8 g of dicyclohexylmethylamine and 25 g of dioxane, and they were heated at 80° C. with stirring, reacted for 5 hours and cooled. The reaction mixture was analyzed by $^1$H-NMR to find that it contained 15% of cyclohexyl N,N-dimethacryloyl carbamate which was the by-product, based on the amount of cyclohexyl N-methacryloyl carbamate which was the intended product.

The reaction mixture was then filtered and concentrated, and the concentrate was purified by column chromatography, to obtain 5.1 g of a white solid having a melting point of 82° C. The yield was 48%.

Example 3

Into a 100 ml reaction vessel were charged 8.7 g of 2-methylcyclohexyl carbamate, 5.3 g of methacryloyl chloride, 9.8 g of dicyclohexylmethylamine and 25 g of heptane, and they were heated at 80° C. with stirring, reacted for 6 hours and cooled. The reaction mixture was analyzed by $^1$H-NMR to find that it contained 11% of 2-methylcyclohexyl N,N-dimethacryloyl carbamate which was the by-product, based on the amount of 2-methylcyclohexyl N-methacryloyl carbamate which was the intended product.

The reaction mixture was then filtered and concentrated, and the concentrate was purified by column chromatography, to obtain 4.8 g of a white solid having a melting point of 65° C. The yield was 46%.

Example 4

Into a 100 ml reaction vessel were charged 8.7 g of 2-butyl carbamate, 5.3 g of methacryloyl chloride, 9.8 g of dicyclohexylmethylamine and 25 g of heptane, and they were heated at 80° C. with stirring, reacted for 6 hours and cooled. The reaction mixture was analyzed by $^1$H-NMR to find that it contained 12% of 2-butyl N,N-dimethacryloyl carbamate which was the by-product, based on the amount of 2-butyl N-methacryloyl carbamate which was the intended product.

The reaction mixture was then filtered and concentrated, and the concentrate was purified by column chromatography, to obtain 4.5 g of a white solid having a melting point of 53° C. The yield was 49%.

Example 5

Into a 100 ml reaction vessel were charged 8.7 g of 2-octyl carbamate, 7.4 g of methacryloyl chloride, 13.7 g of dicyclohexylmethylamine and 25 g of hexane, and they were heated at 80° C. with stirring, reacted for 8 hours and cooled. The reaction mixture was analyzed by $^1$H-NMR to find that it contained 11% of 2-octyl N,N-dimethacryloyl carbamate which was the by-product, based on the amount of 2-octyl N-methacryloyl carbamate which was the intended product.

The reaction mixture was then filtered and concentrated, and the concentrate was purified by column chromatography, to obtain 8.0 g of a white solid having a melting point of 41° C. The yield was 66%.

Example 6

Into a 100 ml reaction vessel were charged 9.5 g of 2-hexyloxyethyl carbamate, 5.3 g of methacryloyl chloride, 6.5 g of diisopropylethylamine and 25 g of hexane, and they were heated at 80° C. with stirring, reacted for 8 hours and cooled. The reaction mixture was analyzed by $^1$H-NMR to find that it contained 46% of 2-hexyloxyethyl N,N-dimethacryloyl carbamate which was the by-product, based on the amount of 2-hexyloxyethyl N-methacryloyl carbamate which was the intended product.

The reaction mixture was then filtered and concentrated, and the concentrate was purified by column chromatography; to obtain 6.4 g of a white solid having a melting point of 25° C. The yield was 37%.

Example 7

Into a 100 ml reaction vessel were charged 9.5 g of 2-hexyloxylethyl carbamate (1e), 5.3 g of methacryloyl chloride (2), 9.8 g of dicyclohexylmethylamine (5) and 25 g of hexane, and they were heated at 80° C. with stirring, reacted for 6 hours and cooled. The reaction mixture was analyzed by $^1$H-NMR to find that it contained 14% of 2-hexyloxyethyl N,N-dimethacryloyl carbamate (4e) which was the by-product, based on the amount of 2-hexyloxyethyl N-methacryloyl carbamate (3e) which the intended product.

The reaction mixture was then filtered and concentrated, and the concentrate was purified by column chromatography, to obtain 4.8 g of a white solid having a melting point of 25° C. The yield was 41%.

Examples 8 to 14

N-acyl carbamates were obtained in the same manner as in Example 7 except that the amounts of 2-hexyloxyethyl carbamate (1e), methacrylic chloride (2) and dicyclohexylmethylamine (5), and the reaction conditions were changed as shown in the following Table 1. The ratio of the amount of 2-hexyloxyethyl N,N-dimethacryloyl carbamate (4e) which is the by-product to the amount of 2-hexyloxyethyl N-methacryloyl carbamate (3e) which is the intended product, and the yield of the intended product are shown in Table 1.

TABLE 1

| Ex. | Reactant | | | Reaction condition | | | Result | |
|---|---|---|---|---|---|---|---|---|
| No. | 1e | 2 | 5 | Solvent (amount) | Temperature | Time | 4e/3e | Yield |
| 8 | 7.6 g | 4.2 g | 7.8 g | Dioxane (20 g) | 80° C. | 6 h | 40% | 31% |
| 9 | 7.6 g | 4.2 g | 7.8 g | Dioxane (20 g) | 100° C. | 5 h | 44% | 27% |
| 10 | 7.6 g | 4.2 g | 7.8 g | Heptane (20 g) | 100° C. | 5 h | 18% | 38% |

TABLE 1-continued

| Ex. | Reactant | | | Solvent (amount) | Reaction condition | | Result | |
|---|---|---|---|---|---|---|---|---|
| No. | 1e | 2 | 5 | | Temperature | Time | 4e/3e | Yield |
| 11 | 7.6 g | 4.2 g | 7.8 g | Toluene (20 g) | 100° C. | 5 h | 50% | 26% |
| 12 | 7.6 g | 4.2 g | 7.8 g | Heptane (10 g) | 80° C. | 3 h | 20% | 39% |
| 13 | 7.6 g | 4.2 g | 15.6 g | Heptane (20 g) | 80° C. | 6 h | 15% | 40% |
| 14 | 7.6 g | 6.3 g | 11.7 g | Heptane (20 g) | 80° C. | 8 h | 23% | 53% |

Comparative Example 1

Into a 100 ml reaction vessel were charged 9.5 g of 2-hexyloxyethyl carbamate, 5.3 g of methacryloyl chloride, 5.1 g of triethylamine and 25 g of hexane, and they were heated at 80° C. with stirring, reacted for 3 hours and cooled. The reaction mixture was analyzed by $^1$H-NMR to find that it contained 275% of 2-hexyloxyethyl N,N-dimethacryloyl carbamate (yield 33%) which was the by-product, based on the amount of 2-hexyloxyethyl N-methacryloyl carbamate (yield 12%) which was the intended product.

Comparative Example 2

Into a 100 ml reaction vessel were charged 9.5 g of 2-hexyloxyethyl carbamate, 5.3 g of methacryloyl chloride, 15.2 g of N-methylmorpholine and 25 g of dioxane, and they were heated at 80° C. with stirring, reacted for 3 hours and cooled. The reaction mixture was analyzed by $^1$H-NMR to find that it contained 2-hexyloxyethyl N,N-dimethacryloyl carbamate (yield 84%) which was the by-product, but did not contain the intended product.

Preparation Example 1

Synthesis of Methyl N,N-dimethacryloyl Carbamate

Into a 2L flask equipped with a mechanical stirrer, dropping funnel and thermometer, were charged 44.5 g of methylcarbamate, 131.8 g of triethylamine and 800 ml of dichloroethane, and they were stirred at room temperature under a nitrogen atmosphere. Then, to this was added dropwise the solution obtained by dissolving 130.1 g of methacrylic chloride into 200 ml of dichloromethane. After completion of the dropping, an oil bath was installed, and the mixture was heated at 75° C. and stirred for 3 hours. After completion of the reaction, the resulted mixture was filtered, and the filtrate was concentrated by a rotary evaporator, purified by vacuum distillation (84° C. (0.23 mmHg)) to obtain methyl N,N-dimethacryloyl carbamate (hereinafter, referred to as "D-MAC")(yield 66%) which was the intended compound.

$^1$H-NMR data of D-MAC (CDCl$_3$, 360 MHz) δ; 1.99 (s, 6H, CH$_2$=C(CH$_3$)—), 3.84 (s, 3H, —OCH$_3$), 5.65 (s, 2H, CH$_2$=C), 5.75 (s, 2H, CH$_2$=C)

IR data of D-MAC (cm$^{-1}$)

1780 (sh, CO), 1750 (CO), 1720 (CO), 1700 (CO), 1630 (C=C), 1440, 1260, 1150

Example 15

Synthesis of Methyl N-methacryloyl Carbamate Using Methyl N,N-dimethacryloyl Carbamate as Raw Material Into a 100 ml eggplant-shape flask were charged 5.0 g of D-MAC, 1.78 g of methyl carbamate and 50 mg of 2,6-di-tert-butylhydroquinone, and they were heated at 120° C. in an oil bath under a nitrogen atmosphere. After heating for 1 hour, the reaction was completed to obtain methyl N-methacryloyl carbamate which was the intended compound (hereinafter, referred to as "N-MAC") at a yield of 23%.

Melting point, and $^1$H-NMR spectrum data of N-MAC m.p.; 94° to 95° C.

$^1$H-NMR (CDCl$_3$); δ2.0 (s, 3H, CH$_2$=C(CH$_3$)—), 3.86 (s, 3H, —OCH$_3$), 5.62 (s, 2H, CH$_2$=C), 5.81 (s, 2H, CH$_2$=C)

Example 16

Into a 100 ml eggplant-shape flask were charged 2.11 g of D-MAC, 0.75 g of methyl carbamate, 95 mg of p-toluenesulfonic acid and 20 mg of 2,6-di-tert-butylhydroquinone, and they were heated at 110° C. under a nitrogen atmosphere. After heating for 1 hour, the reaction was completed to obtain N-MAC at a yield of 87%.

Example 17

Into a 100 ml eggplant-shape flask were charged 2.11 g of D-MAC, 0.75 g of methyl carbamate, 58 mg of 85% phosphoric acid and 20 mg of 2,6-di-tert-butylhydroquinone, and they were heated at 110° C. under a nitrogen atmosphere. After heating for 1 hour, the reaction was completed to obtain N-MAC at a yield of 85%.

Example 18

Into a 100 ml eggplant-shape flask were charged 2.11 g of D-MAC, 0.75 g of methyl carbamate, 58 mg of 85% phosphoric acid, 20 mg of 2,6-di-tert-butylhydroquinone and 6.86 g of xylene, and they were heated at 110° C. under a nitrogen atmosphere. After heating for 1.5 hours, the reaction was completed to obtain N-MAC at a yield of 60%.

Example 19

Into a 100 ml eggplant-shape flask were charged 2.11 g of D-MAC, 0.75 g of methyl carbamate, 58 mg of 85% phosphoric acid, 20 mg of 2,6-di-tert-butylhydroquinone and 6.86 g of diglyme, and they were heated at 110° C. under a nitrogen atmosphere. After heating for 1.5 hours, the reaction was completed to obtain N-MAC at a yield of 50%.

Example 20

Into a 100 ml eggplant-shape flask were charged 2.11 g of D-MAC, 0.75 g of methyl carbamate, 58 mg of 85% phosphoric acid, 20 mg of 2,6-di-tert-butylhydroquinone and 6.86 g of butyl acetate, and they were heated at 110° C. under a nitrogen atmosphere. After heating for 1.5 hours, the reaction was completed to obtain N-MAC at a yield of 50%.

Example 21

Into a 100 ml eggplant-shape flask were charged 2.11 g of D-MAC, 0.75 g of methyl carbamate, 58 mg of 85% phosphoric acid, 20 mg of 2,6-di-tert-butylhydroquinone and 6.86 g of (o)-dichlorobenzene, and they were heated at 110° C. under a nitrogen atmosphere. After heating for 1.5 hours, the reaction was completed to obtain N-MAC at a yield of 69%.

Example 22

Into a reaction vessel were charged 1.0 g (4.73 mmol) of D-MAC, and 4.7 g of dioxane. 0.346 g (4.73 mmol) of n-butylamine was then dropwize added to the reaction vessel with stirring under nitrogen atmosphere at a room temperature. After one day, a solvent was removed from the reaction mixture by evapolaring. The resulting colorless oil was placed in a silica gel column and eluted by using ethyl acetate/hexane (3/2). N-MAC which was white solid and N-(n-butyl)methacrylamide which was colorless oil were obtained. The yield thereof were 88% and 63%, respectively.

Example 23

Into a reaction vessel were charged 2.0 g (9.52 mmol) of D-MAC, and 5.0 g of dioxane. 0.84 g of 25% aqueous ammonia (12.4 mmol of $NH_3$) was then dropwize added to the reaction vessel with stirring under nitrogen atmosphere at a room temperature. After one day, a solvent was removed from the reaction mixture by evapolaring. The resulting colorless oil was analyzed by using high pressure liquid chromatography (HPLC). The yield of N-MAC was 80%.

Example 24

Into a reaction vessel were charged 2.11 g (10.0 mmol) of D-MAC, and 5.0 g of methanol. 0.68 g of 25% aqueous ammonia (10.0 mmol of $NH_3$) was then dropwize added to the reaction vessel with stirring under nitrogen atmosphere at a room temperature. After one day, a solvent was removed from the reaction mixture by evapolaring. The resulting colorless oil was analyzed by using HPLC. The yield of N-MAC was 100%.

Example 25

Into a reaction vessel were charged 2.0 g (9.52 mmol) of D-MAC, and 5.0 g of dioxane. 2.64 g of 20% aqueous sodium hydroxide (117.3 mmol of NaOH) was then dropwize added to the reaction vessel with stirring under nitrogen atmosphere at a room temperature. After one day, a solvent was removed from the reaction mixture by evapolaring. The resulting colorless oil was analyzed by using HPLC. The yield of N-MAC was 46%.

Example 26

Into a reaction vessel were charged 2.11 g (10.0 a mol) of D-MAC, and 3.0 g of methanol. 2.0 g of 20% methanol solution of sodium hydroxide (112.5 mmol of NaOH) was then dropwize added to the reaction vessel with stirring under nitrogen atmosphere at a room temperature. After one day, a solvent was removed from the reaction mixture by evapolaring. The resulting colorless oil was analyzed by using HPLC. The yield of N-MAC was 31%.

Example 27

Into a reaction vessel were charged 2.0 g (9.52 mmol) of D-MAC, and 5.0 g of dioxane. 1.05 g of aqueous dimethylamine (11.7 mmol of $NH(CH_3)_2$) was then dropwize added to the reaction vessel with stirring under nitrogen atmosphere at a room temperature. After one day, a solvent was removed from the reaction mixture by evapolaring. The resulting colorless oil was analyzed by using HPLC. The yield of N-MAC was 83%.

What is claimed is:

1. A method for producing the N-acyl carbamate represented by the formula:

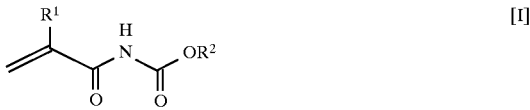

wherein, $R^1$ is a hydrogen atom or a lower alkyl group, and $R^2$ is a residual group obtained by removing a hydroxyl group from a monovalent alcohol; which comprises the step of reacting the N,N-diacyl carbamate represented by the formula:

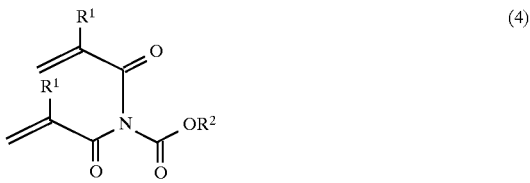

wherein, $R^1$ and $R^2$ are the same as defined above; with the active hydrogen compound represented by the formula:

wherein, X is a nitrogen atom or an oxygen atom, Y is a hydrogen atom, a linear or cyclic alkyl group, aryl group, aralkyl group, alkenyl group, alkynyl group, linear or cyclic alkylcarbonyl group, arylcarbonyl group, aralkylcarbonyl group, alkenylcarbonyl group, alkynylcarbonyl group, or alkoxycarbonyl group, having 1 to 18 carbon atoms, which may have a substituent, and n is an integer from 1 to k, wherein k indicates a valence of the X atom.

2. The method according to claim 1, wherein the active hydrogen compound is the amine compound represented by the formula:

wherein, $R^4$ is a linear or cyclic alkyl group, aryl group, aralkyl group, alkenyl group, or alkynyl group, having 1 to 18 carbon atoms, which may have a substituent, and m is an integer from 1 to 3.

3. The method according to claim 1, wherein the active hydrogen compound is the carbamate represented by the formula:

wherein, $R^2$ is a linear or cyclic alkyl group, aryl group, aralkyl group, alkenyl group, or alkynyl group, having from 1 to 18 carbon atoms, which may have a substituent.

4. The method according to claim 3, wherein the reaction is conducted in the presence of an acidic catalyst.

5. A method for producing the N-acyl carbamate represented by the formula:

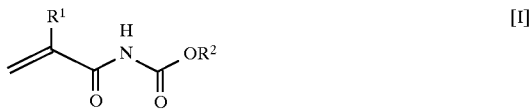

wherein, $R^1$ is a hydrogen atom or an alkyl group having 1 to 6 carbon atoms, and $R^2$ is a linear or cyclic alkyl group, aryl group, aralkyl group, alkenyl group, or alkynyl group, having from 1 to 18 carbon atoms, which may have a substituent; which comprises the step of reacting the N,N-diacyl carbamate represented by the formula:

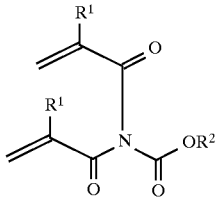 (4)

wherein, $R^1$ and $R^2$ are the same as defined above; with the active hydrogen compound represented by the formula:

$$H_n XY_{k-n} \quad (5)$$

wherein, X is a nitrogen atom or an oxygen atom, Y is a hydrogen atom, a linear or cyclic alkyl group, aryl group, aralkyl group, alkenyl group, alkynyl group, linear or cyclic alkylcarbonyl group, arylcarbonyl group, aralkylcarbonyl group, alkenylcarbonyl group, alkynylcarbonyl group, or alkoxycarbonyl group, having 1 to 18 carbon atoms, which may have a substituent, and n is an integer from 1 to k, wherein k indicates a valence of the X atom.

6. The method according to claim 5, wherein the active hydrogen compound is the amine compound represented by the formula:

$$H_m NR^4_{3-m} \quad (6)$$

wherein, $R^4$ is a linear or cyclic alkyl group, aryl group, aralkyl group, alkenyl group, or alkynyl group, having 1 to 18 carbon atoms, which may have a substituent, and m is an integer from 1 to 3.

7. The method according to claim 5, wherein the active hydrogen compound is the carbamate represented by the formula:

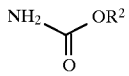 (2)

wherein, $R^2$ is a linear or cyclic alkyl group, aryl group, aralkyl group, alkenyl group, or alkynyl group, having from 1 to 18 carbon atoms, which may have a substituent.

8. The method according to claim 7, wherein the reaction is conducted in the presence of an acidic catalyst.

* * * * *